United States Patent [19]

Bova et al.

[11] Patent Number: 4,934,377

[45] Date of Patent: Jun. 19, 1990

[54] INTRAOPERATIVE NEUROELECTROPHYSIOLOGICAL MONITORING SYSTEM

[75] Inventors: Joseph A. Bova, Eastlake, Ohio; Richard L. Prass, Virginia Beach, Va.

[73] Assignee: The Cleveland Clinic Foundation, Cleveland, Ohio

[21] Appl. No.: 124,822

[22] Filed: Nov. 24, 1987

[51] Int. Cl.$^5$ .............................................. A61B 5/04
[52] U.S. Cl. ................................. 128/696; 606/34
[58] Field of Search ........... 128/303.1, 303.13–303.19, 128/419 R, 419 PT, 419 P, 421–423, 695–712, 731, 741; 606/32–40

[56] References Cited

U.S. PATENT DOCUMENTS

| | | | |
|---|---|---|---|
| 3,703,900 | 11/1972 | Holznagel | 128/419 P |
| 3,857,398 | 12/1974 | Rubin | 128/697 |
| 3,933,157 | 1/1976 | Bjurwill et al. | 128/303.14 |
| 3,960,141 | 6/1976 | Bolduc | 128/303.13 |
| 4,184,492 | 1/1980 | Meinke et al. | 128/303.14 |
| 4,200,104 | 4/1980 | Harris | 128/303.14 |
| 4,235,242 | 11/1980 | Howson et al. | 128/695 |
| 4,294,245 | 10/1981 | Bussey | 604/20 |
| 4,331,157 | 5/1982 | Keller, Jr. et al. | 128/419 R |
| 4,374,517 | 2/1983 | Hagiwara | 128/303.15 |
| 4,469,098 | 9/1984 | Davi | 128/395 |
| 4,487,489 | 12/1984 | Takamatsu | 128/6 |
| 4,517,976 | 5/1985 | Murakoshi et al. | 128/303.17 |
| 4,565,200 | 1/1986 | Cosman | 128/303.18 |
| 4,576,178 | 3/1986 | Johnson | 128/696 |

FOREIGN PATENT DOCUMENTS 56235  7/1982  European Pat. Off. ....... 128/303.15

*Primary Examiner*—Lee S. Cohen
*Assistant Examiner*—David Shay
*Attorney, Agent, or Firm*—D. Peter Hochberg; Mark Kusner; Louis J. Weisz

[57] ABSTRACT

The add-on circuit arrangement permits selective muting of noise signals which are caused by electrosurgery and by a stimulus source during neurophysiological monitoring of a surgical patient. Switches (39, 7 and 24) are provided to select: electrosurgery noise muting; stimulus artifact muting; and to select fixed or variable recorder recovery time. An inductive pickup (12) is coupled to a conductor (11) which carries radiofrequency signals during active periods of electrosurgery. The pickup (12) and associated circuitry (14–17) generate output signals (ES detect signals) which correspond in time to the active periods of electrosurgery. An active output signal of the "1" output of the flip-flop (38) operates the disable switches 44 which are interposed between the monitoring electrodes (41) and the recorder (46). The flip-flop is set by the ES detect signal and reset by selected recovery time signals. Stimulus artifacts are selectively muted by the stimulus disable switch (7), the pulse generator (4) which responds to synchronizing signals from the stimulus source (1) and the AND gate (9).

6 Claims, 1 Drawing Sheet

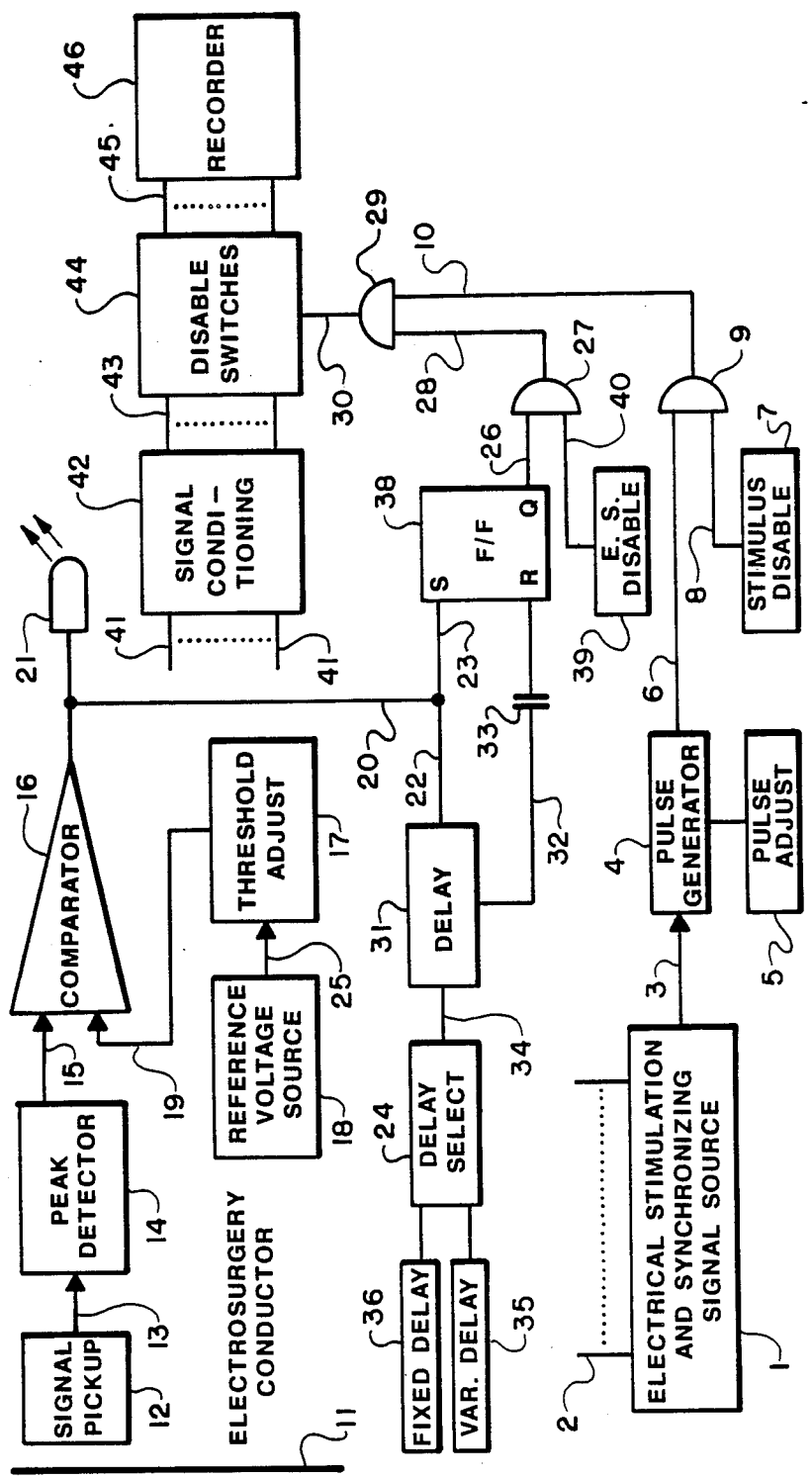

INTRAOPERATIVE NEUROELECTROPHYSIOLOGICAL MONITORING SYSTEM

TECHNICAL FIELD

This invention relates to an "add-on" system for the automatic elimination of noise, due to electrosurgery and electrical stimulation, from electrophysiological signals derived from a surgical patient for the purpose of intraoperative neuroelectrophysiological monitoring.

BACKGROUND ART

Electrosurgery/electrocautery, employed during surgical procedures, creates high amplitude electrical artifacts during intraoperative biophysiological recordings. When displayed acoustically through a loud speaker, electrosurgery/electrocautery artifacts appear as a loud buzz or other annoying sound; and when displayed through an oscilloscope these artifacts clutter the recording. Since these artifacts provide no useful information, it is desirable to eliminate them from or minimize their effects in the recording. There are several prior art arrangements for eliminating electrosurgery/electrocautery artifacts from biophysiological recordings. Among these known arrangements are a footswitch which disables the signal path to the recorder. The footswitch may be independent of the electrosurgery apparatus or it may be included as a hardwired modification of the footswitch of the electrosurgery apparatus. In the case of an independent disable footswitch, a technician with responsibility for the recording and display of the biophysiological signals, operates the switch in anticipation of electrosurgery during a surgical procedure. Such an arrangement requires the technician to have special knowledge of surgical procedures and requires constant and careful observation of the surgery. While the integration of the footswitch into the electrosurgery apparatus is reliable and overcomes the shortcomings of the independent footswitch, the hardwired modification of all of the electrocautery units which may be employed during a surgical procedure is burdensome.

Radiofrequency antennas and/or "in-line" detection devices have been used to detect radiofrequency energy to trigger circuitry to disable recording. An example of such an arrangement is a cardiac doppler device used for intraoperative monitoring of heart functions and "air-embolus" monitoring.

In addition to automatic elimination of signals due to electrosurgery in the recording of biophysiological responses, it is desirable to eliminate the signals which are due to the electrical stimulation signals from the electrophysiological signals derived from a surgical patient. The recording of the electrical stimulation may interfere with the ability to record and/or interpret the intended biophysiological (true) response to the electrical stimulation. The temporal separation between the stimulus and the response and the use of fast recovery amplifiers may permit resolution of the stimulus and the response in oscillographic recorders. However, such resolution is not possible in the case of acoustic recorders. Stimulus artifact elimination has been achieved previously in the design of an acoustic EMG monitoring device e.g., Grass NL-1 Nerve Locator/Monitor. In that apparatus, a synchronous pulse from the electrical stimulus generator triggers a gate circuit which eliminates the period of electrical stimulus presentation from the recorded signal. A variable control allows the muted interval to be adjusted within predetermined limits.

DISCLOSURE OF THE INVENTION

In accordance with this invention, noise signals which represent active periods of electrosurgery or electrocautery during a surgical procedure, are eliminated from the electrophysiological response signals which are delivered to a recorder of an intraoperative neuroelectrophysiological monitoring system. A pickup, which is clamped to and coupled to a conductor which carries radio frequency signals during active periods of electrosurgery, produces corresponding small output signals which are processed to provide "muting output signals" for disabling the recording of electrophysiological response signals from a surgical patient during active periods of electrosurgery and for adjustable brief periods of recovery thereafter. The pickup is typically coupled to a conductor which is connected to the cautery forceps or to the patient plate of electrosurgery apparatus. The invention provides manual controls for selecting the electrosurgery muting function and additional controls for adjusting the period of recovery after termination of the active period. The invention further includes circuitry for disabling the recording of electrophysiological response signals during the occurrence of stimulus artifacts.

THE DRAWING

The single FIGURE of the drawing is a schematic block diagram of a monitoring system in accordance with this invention.

DETAILED DESCRIPTION

The neuroelectrophysiological monitoring system of FIG. 1 includes hand operated switches 7, 39, and 24 which respectively: enable "stimulus artifact muting"; enable "electrosurgery muting"; and select between a "fixed recovery period" and a "variable recovery period" in the case that "electrosurgery muting" has been selected.

The system also includes manual adjustments 5, 17 and 35 which respectively: set the muting period when switch 7 has been operated to select "stimulus artifact muting"; set the threshold of the electrosurgery signal that will initiate "electrosurgery muting" when switch 39 has been operated; and set the recovery period when "electrosurgery muting" and "variable recovery period" are selected.

During periods of neuroelectrophysiological monitoring of a surgical patient, stimuli from the electrical stimulation and synchronizing signal source 1 are conducted to selected sites of a surgical patient by the conductors 2. The resulting electrophysiological response signals are conducted from a patient by the monitoring electrodes 41. As seen in the figure, there are a plurality of stimulus channels 2 and a corresponding plurality of monitoring channels 41. The signals from the monitoring electrodes on conductors 41 are processed in the signal conditioning circuitry 42 to provide signals of the appropriate electrical characteristics for the input of the recorder 46.

The signal source 1 provides synchronizing signals to the pulse generating circuit 4 via the conductor 3. The synchronizing signals are coordinated in time with the stimulus signals. The pulse generating circuit 4, in response to the synchronizing signals, generates corresponding output signals on conductor 6. The duration of the output pulses is adjustable from 0.1 millisecond to 10 milliseconds by means of the pulse width adjustment 5. When the stimulus muting function has been selected by operation of switch 7, the signals on conductors 6 and 8 will enable the AND gate 9 for a period of time substantially equal to the width of the output pulse of the pulse generator 4. The resulting signal on conductor 10 is a Muting signal which serves to operate the disable switches 44. The muting signal is conveyed to the disable switches 44 by the OR gate 29 and conductor 30.

The pickup 12 is clamped to and coupled to the electrosurgery conductor 11 which carries radiofrequency signals when the associated electrosurgery apparatus is active. This arrangement advantageously eliminates the need for a direct electrical connection to the electrosurgery apparatus and permits the use of any available electrosurgery apparatus without modification. Since, any modification of electrosurgery apparatus may involve an unexpected risk, modifications are generally avoided. The pickup may be an inductive pickup; and the electrosurgery conductor 11 may be connected to the cautery forceps or to the patient plate. The pickup receives only a very small portion of energy from the electrosurgery wire 11. The pickup output signal is directed to the peak detector circuit 14 which amplifies the AC signal and converts the amplified signal to a corresponding DC signal. The peak detector 14 produces a smooth DC level which is proportional to the peak value of the output waveform i.e., non-repetitive radiofrequency spectral noise, of any electrosurgery generator. The peak value of the waveform is used to improve low energy signal detection and to provide a fast response time.

The DC signal from the peak detector 14, which is conducted to the comparator 16 via conductor 15, and the reference voltage from the threshold adjust circuit 17 are processed by the comparator 16. The precision reference circuit 18 provides a temperature stable reference voltage output signal; and the threshold adjust circuit 17 is an adjustable output voltage divider. It is necessary to set the muting threshold level to compensate for differences in operating room environment and for differences in electro surgery devices. Typically, at the beginning of a procedure, the surgeon enables the surgery pen while in air removed from the patient and the threshold adjust circuit is adjusted to achieve muting.

When the DC signal from the peak detector 14 exceeds the reference voltage, the comparator 16 generates an active "electrosurgery detected" (ESD) signal on conductor 20. An active ESD signal on conductor 20 sets flip-flop 38 and activates the light emitting diode 21 to provide a visual indication that electrosurgery is in progress. If the switch 39 is closed to activate the electrosurgery muting function, the "Q" output signal of the flip-flop 38 on conductor 26 and the ESD signal on conductor 40 enable AND gate 27. The active output signal of the AND gate 27 is a second muting signal which serves to activate OR gate 29 and thus operate the disable switches 44.

As noted earlier herein, the "select recovery" switch 24 selects circuitry to reset the flip-flop 38 a fixed recovery period of time or an adjustable period of time after termination of the ESD signal. When the fixed recovery time the delay circuit 31 provides a fixed delay of approximately 5 milliseconds. When the adjustable recovery time is selected, the delay circuit 31 provides a variable delay having a duration of 0.5 seconds to 2.5 seconds as established by the adjustment of the control 35. A positive going transition of a pulse on conductor 32 resets the flip-flop 38 at the end of the selected recovery time.

By way of example, the delay circuit 31 may be a monostable pulse generator circuit which responds to a negative going input signal from conductor 20. Such a signal occurs when the ESD signal terminates. In response to negative going input signal, the circuit 31 generates a negative going output signal on conductor 32. The output signal has a duration as described above herein. After the selected period of delay, the output signal on conductor 32 goes positive. That positive going signal is coupled to the reset terminal of the flip-flop 38 by the capacitor 33.

The above arrangements are illustrative of the claimed invention and many changes in implementation may be made without departing from the spirit and scope of the invention.

What is claimed is:

1. An intraoperative neuroelectrophysiological monitoring system, for use with an electrosurgery apparatus used in the treatment of a surgical patient, for recording biophysical responses resulting from electrical stimulation of a surgical patient from electrical stimulation signals, said monitoring system comprising:
    means for coupling said electrical stimulation signals to selected sites of a surgical patient;
    one or more monitoring electrodes for deriving electrophysiological response signals from a surgical patient;
    recording means for displaying biophysical responses corresponding to electrophysical response signals derived from a surgical patient;
    means for connecting said monitoring electrodes to said recording means;
    pick-up means for connection to a conductor of said electrosurgery apparatus for receiving signal samples for the energy generated by the electrosurgery apparatus during an electrosurgery procedure; and
    first control means connected to said pickup means and responsive to said electrosurgery signal samples for generating first muting signals for selectively disabling said recording means during periods of time coordinated to the time periods of electrosurgery procedures.

2. An intraoperative neuroelectrophysiological monitoring system in accordance with claim 1 wherein said pickup means is inductively coupled to said conductor.

3. An intraoperative neuroelectrophysiological monitoring system in accordance with claim 1 wherein the time periods of said first muting signals extend beyond the termination of the corresponding time periods of said electrosurgery procedures; and said first control means comprises means for adjusting the time periods of said first muting signals.

4. An intraoperative neuroelectrophysiological monitoring system in accordance with claim 1 wherein said system further comprises:
    a source of synchronizing signals directly related in time to said stimulation signals; and second control means connected to said source of synchronizing signals for generating second muting signals for selectively disabling said recording means during periods of time coordinated to the time periods of said stimulation signals.

5. An intraoperative neuroelectrophysiological monitoring system in accordance with claim 6 wherein said second control means comprises means for controlling the time periods of said second muting signals.

6. An intraoperative neuroelectrophysiological monitoring system for recording biophysical responses resulting from electrical stimulation of a surgical patient comprising:

a source of electrical stimulation signals and means for coupling said signals to selected sites of a surgical patient; one or more monitoring electrodes for deriving electrophysiological response signals from a surgical patient;

recording means coupled to said monitoring electrodes for displaying biophysical responses corresponding to the electrophysiological response signals derived from a surgical patient;

pickup means for connection to a conductor of electrosurgery apparatus used in the treatment of a monitored surgical patient for receiving signal samples of the energy generated by the electrosurgery apparatus during an electrosurgery procedure;

control means connected to said pickup means and responsive to electrosurgery signal samples for selectively disabling said recording means during electrosurgery procedures.

* * * * *